US008064062B2

(12) United States Patent
Ogawa (10) Patent No.: US 8,064,062 B2
(45) Date of Patent: Nov. 22, 2011

(54) PHOTOMETRIC APPARATUS AND AUTOMATIC ANALYZER

(75) Inventor: Yuji Ogawa, Shizuoka-ken (JP)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 12/613,422

(22) Filed: Nov. 5, 2009

(65) Prior Publication Data

US 2010/0045994 A1 Feb. 25, 2010

Related U.S. Application Data

(63) Continuation of application No. PCT/JP2008/058364, filed on May 1, 2008.

(30) Foreign Application Priority Data

May 9, 2007 (JP) ................................ 2007-124678

(51) Int. Cl.
*G01N 21/00* (2006.01)
(52) U.S. Cl. ........................................ 356/436; 356/432
(58) Field of Classification Search .......... 356/432–444, 356/246, 71–72; 422/63–67, 82.01, 99; 435/289, 435/291
See application file for complete search history.

(56) References Cited

U.S. PATENT DOCUMENTS

| 4,498,780 | A | * | 2/1985 | Banno et al. | 356/414 |
| 4,528,159 | A | * | 7/1985 | Liston | 422/65 |
| 4,685,801 | A | * | 8/1987 | Minekane | 356/328 |
| 4,695,727 | A | * | 9/1987 | Brierley et al. | 250/328 |
| 4,826,319 | A | * | 5/1989 | Namba et al. | 356/339 |
| 4,950,077 | A | | 8/1990 | Manabe | |
| 4,980,292 | A | * | 12/1990 | Elbert et al. | 422/63 |
| 5,307,144 | A | * | 4/1994 | Hiroshi et al. | 356/244 |
| 6,737,021 | B2 | * | 5/2004 | Watari et al. | 422/63 |

FOREIGN PATENT DOCUMENTS

| JP | 06-19079 Y2 | 5/1994 |
| JP | 08-122247 A | 5/1996 |
| JP | 10-080416 A | 3/1998 |
| JP | 10-115583 A | 5/1998 |
| JP | 2002-267595 A | 9/2002 |

* cited by examiner

*Primary Examiner* — Sang Nguyen
(74) *Attorney, Agent, or Firm* — Kilpatrick Townsend & Stockton LLP (57) ABSTRACT

A photometric apparatus and an automatic analyzer in which liquid samples contained in vessels are measured with light of different wavelengths while the vessels are transferred are provided. A photometric apparatus includes light sources that are arranged in the movement direction of a vessel and emit light of different wavelengths, light-receiving devices that are located opposing the light sources with the vessels interposed inbetween and receive light of different wavelengths emitted from the light sources. The arrangement length of light sources along the movement direction of the vessels is shorter than the arrangement pitch of the vessels.

7 Claims, 6 Drawing Sheets

PHOTOMETRIC APPARATUS AND AUTOMATIC ANALYZER

CROSS-REFERENCE TO RELATED APPLICATIONS

This application is a continuation of PCT international application Ser. No. PCT/JP2008/058364, filed on May 1, 2008 which designates the United States, incorporated herein by reference, and which claims the benefit of priority from Japanese Patent Application No. 2007-124678, filed on May 9, 2007, the entire contents of which are incorporated herein by reference.

BACKGROUND OF THE INVENTION

1. Field of the Invention

The present invention relates to a photometric apparatus and an automatic analyzer.

2. Description of the Related Art

Conventional automatic analyzers use photometric apparatuses that measure, using light of different wavelengths depending on what is to be measured, a reaction liquid in which a reagent and a test liquid react. An example of such automatic analyzers is a pre-spectroscopic automatic analyzer (e.g., see Japanese Utility Model Application Laid-open No. H6-19079) in which light sources respectively emitting light of different wavelengths and light-receiving devices are located opposing each other and along an arrangement direction. The center angles among the light sources or light-receiving devices are the same as the center angle among reaction vessels set on a cuvette wheel. The automatic analyzer intermittently rotates the cuvette wheel to transfer the reaction vessels, which then cut across light axes of light of different wavelengths emitted from the light sources. On the basis of the light absorbance of the reaction liquid, the automatic analyzer analyzes a constituent concentration and the like of a specimen.

In the pre-spectroscopic automatic analyzer disclosed in Japanese Utility Model Application Laid-open No. H6-19079, light is dispersed into light of different wavelengths and then emitted from the light sources. When the automatic analyzer in Japanese Utility Model Application Laid-open No. H6-19079 intermittently rotates the cuvette wheel, a problem occurs in that some reaction vessels cut across only light axes of light of different wavelengths emitted from part of light sources. For example, in a photometric apparatus shown in FIG. 9, light sources L1-L5 respectively emit light (of wavelengths λ1-λ5), and light transmitted through a liquid contained in a reaction vessel C is received by the light-receiving devices R1-R5.

Figure 9:
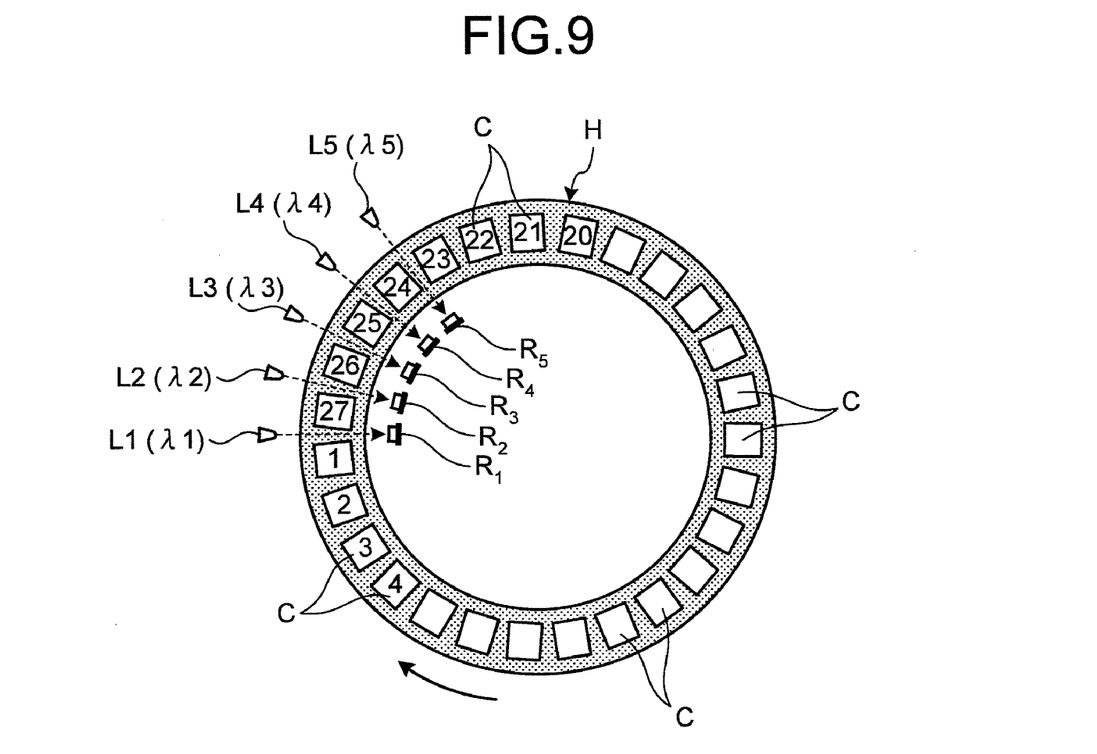
FIG. 9 is a schematic diagram of a cuvette wheel and an analysis optical system for illustrating a measurement method of a conventional photometric apparatus.
Figure 10:
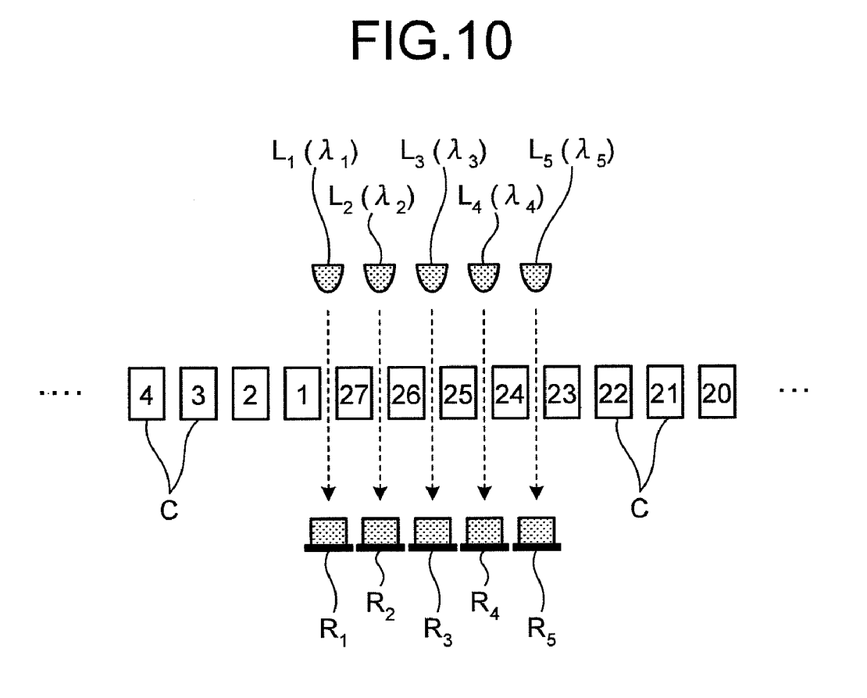
FIG. 10 is a schematic diagram in which positions of LEDs and light-receiving devices constituting the photometric apparatus shown in FIG. 9 and of reaction vessels are viewed from the inside of a cuvette wheel with the reaction vessels being arranged in a straight line.

In the photometric apparatus shown in FIG. 9, suppose, for convenience of the description, that Nos. 1-27 are attached to reaction vessels C and arranged in the counterclockwise direction, that the 27 reaction vessels C are arranged on a cuvette wheel H, and that one intermittent rotation transfers a portion of the reaction vessels, i.e., seven reaction vessels C. Considering the rotation direction of the cuvette wheel H, No. 1 reaction vessel C is positioned right in front of the light source L1 and the light-receiving device R1. FIG. 10 is a schematic diagram in which positions of the light sources L1-L5, the light-receiving devices R1-R5, and the reaction vessels C before the cuvette wheel H is rotated are viewed from the inside of the cuvette wheel H, and the reaction vessels C are arranged in a straight line.

Figure 11:
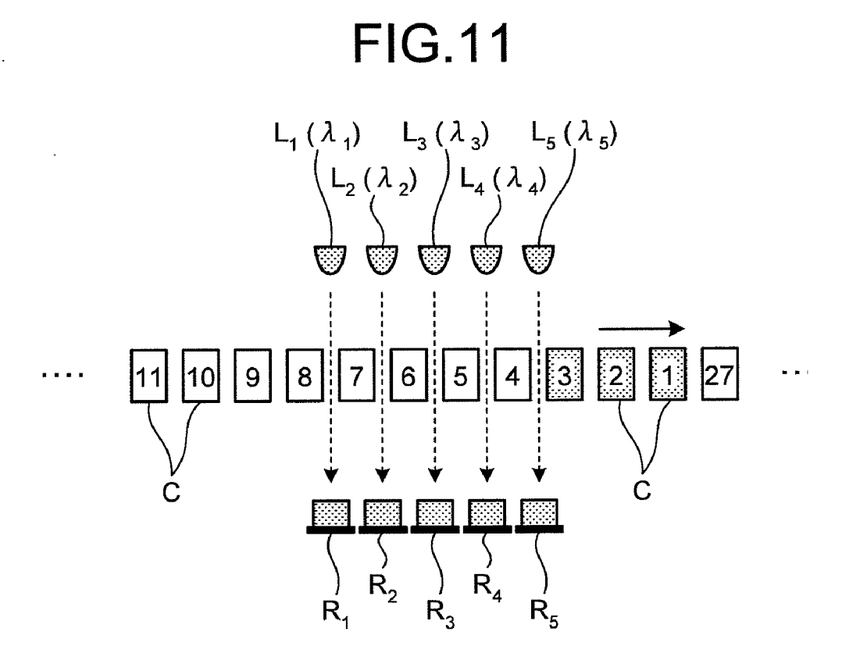
FIG. 11 is a schematic diagram illustrating a state after a cuvette wheel in a state in FIG. 10 is intermittently rotated.

To measure optical characteristics of liquids contained in the reaction vessels C, the cuvette wheel H in a state in FIG. 10 is rotated by one intermittent rotation in the clockwise direction, as represented by the arrow. Then, the reaction vessels C arranged on the cuvette wheel H are transferred to the right by seven units as shown in FIG. 11. As a result, Nos. 1-3 reaction vessels C cross the light sources L1-L5 so that the measurement of the optical characteristics of the liquids is completed with light of different wavelengths (wavelength λ1-λ5). Nos. 4-7 reaction vessels C, however, cross only some light sources emitting part of different wavelengths, and the measurement of the optical characteristics of the liquids may not be completed.

For example, when the light sources L1 and L2 and the light-receiving devices R1 and R2 are used to take a measurement, the measurement of the optical characteristics is completed for Nos. 1-6 reaction vessels C but not completed for No. 7 reaction vessel C as shown in FIG. 11.

SUMMARY OF THE INVENTION

A photometric apparatus according to one aspect of the present invention is used in an automatic analyzer that measures an optical characteristic of liquids contained in vessels with light of different wavelengths while transferring the vessels. The photometric apparatus includes: light sources that are arranged in a movement direction of the vessel and respectively emit light of different wavelengths; and light-receiving devices that are located opposing to the light sources with the vessel interposed inbetween and receive light of different wavelengths emitted from the light sources, wherein an arrangement length of the light sources along the movement direction of the vessel is shorter than an arrangement pitch of the vessel.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
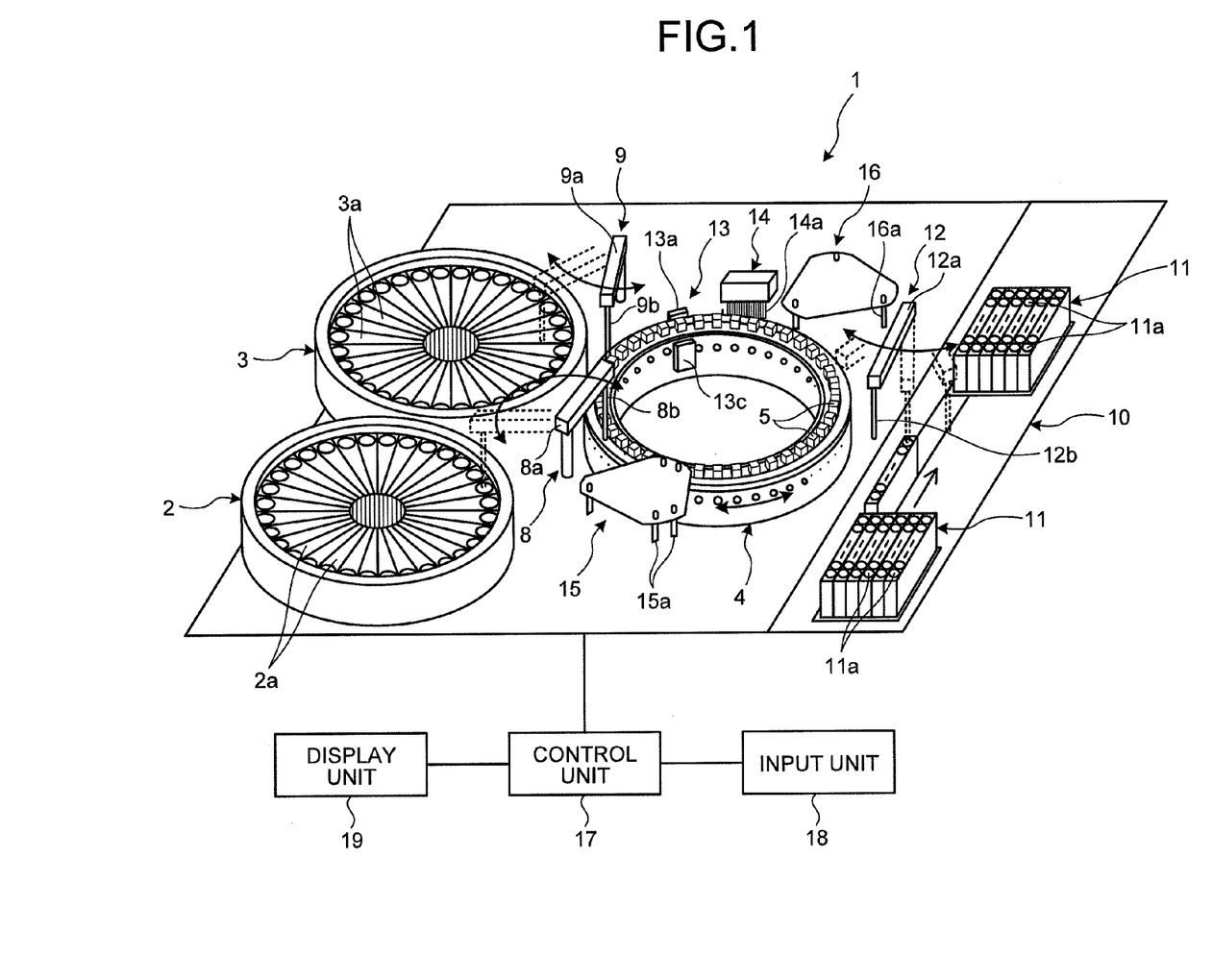
FIG. 1 is a schematic diagram of a configuration of an automatic analyzer in accordance with a first embodiment.
Figure 2:
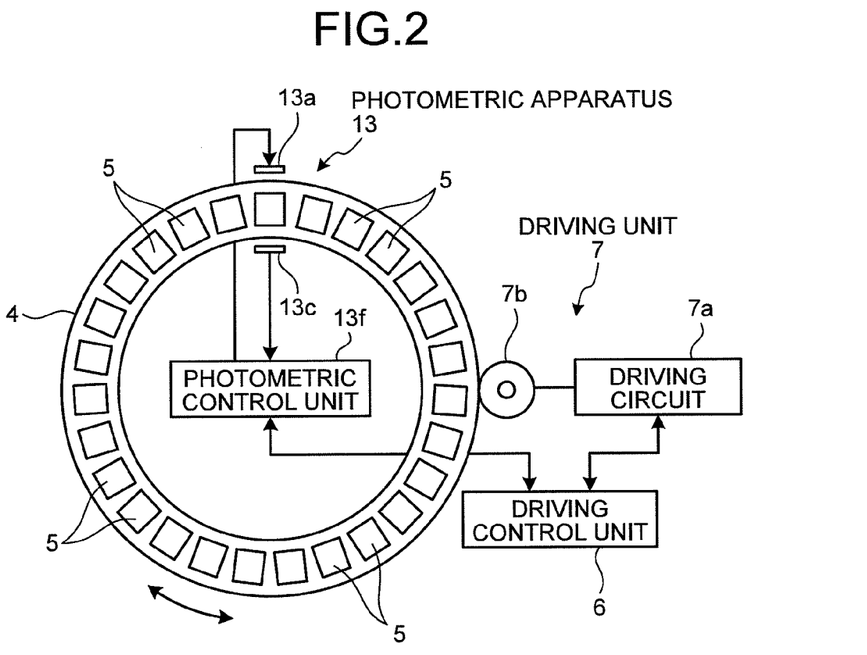
FIG. 2 is a schematic diagram illustrating a photometric apparatus of the present invention together with a cuvette wheel, a driving control unit, and a driving unit.

A photometric apparatus and an automatic analyzer in accordance with a first embodiment of the present invention are described in detail with reference to drawings. FIG. 1 is a schematic diagram of a configuration of an automatic analyzer in accordance with a first embodiment. FIG. 2 is a schematic diagram illustrating a photometric apparatus of the present invention together with a cuvette wheel, a driving control unit, and a driving unit.

As shown in FIG. 1, an automatic analyzer 1 includes reagent tables 2 and 3, a cuvette wheel 4, a specimen-vessel transferring system 10, a photometric apparatus 13, a washing system 14, a first stirrer 15, a second stirrer 16, and a control unit 17.

As shown in FIG. 1, in the reagent tables 2 and 3, reagent vessels 2a for a first reagent and reagent vessels 3a for a second reagent are arranged along the circumferential direction. The reagent tables 2 and 3 are rotated by a driving unit and transfer the reagent vessels 2a and 3a in the circumferential direction. The reagent vessels 2a and 3a are filled with predetermined reagents corresponding to examination items. Identification code labels (not shown) indicating information such as a type, lot, and expiration date of a reagent are attached to the outer surface of the reagent vessels 2a and 3a. A reading apparatus that reads reagent information stored in the identification code labels attached to the reagent vessels 2a and 3a and outputs the reagent information to the control unit 17 is located in the outer circumference of the reagent tables 2 and 3.

As shown in FIG. 1, reaction vessels 5 are arranged on the cuvette wheel 4 along the circumferential direction, and the cuvette wheel 4 is intermittently rotated by a pulse motor 7b (see FIG. 2) in the direction shown in the arrow so as to transfer the reaction vessels 5 in the circumferential direction. For example, as shown in FIG. 2, the cuvette wheel 4 holds twenty-seven reaction vessels 5, and moves the reaction vessels 5 by seven units for one intermittent rotation, and four intermittent rotations result in "one revolution" plus "one vessel". The cuvette wheel 4 includes holders that hold the reaction vessels 5, and light paths that are circle apertures through which light emitted from each LED 13b (see FIG. 3) in an LED array 13a is transmitted to each corresponding light-receiving device 13d (see FIG. 3) in a light-receiving device array 13c.

The holders are arranged on the outer circumference of the cuvette wheel 4 along the circumferential direction at predetermined intervals. The holders include light paths in radial directions. Operations of the cuvette wheel 4 are controlled by a driving unit 7. As shown in FIG. 2, the driving unit 7 includes a driving circuit 7a and the pulse motor 7b that rotates the cuvette wheel 4. The driving unit 7 controls the driving of the pulse motor 7b by a driving control unit 6 that uses a CPU and the like with the driving circuit 7a so that the intermittent rotation of the cuvette wheel 4 is controlled.

Figure 3:
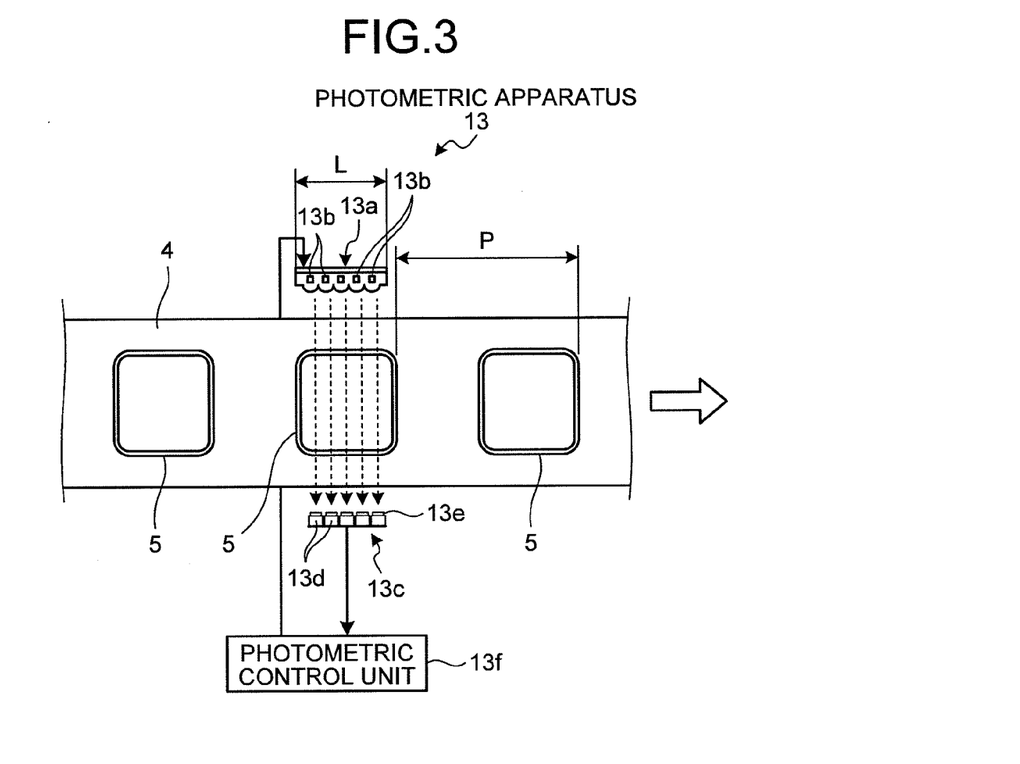
FIG. 3 is a schematic diagram in which positions of LEDs and light-receiving devices constituting a photometric apparatus and of reaction vessels are viewed from an inside of a cuvette wheel with the reaction vessels being arranged in a straight line.

FIG. 3 is a schematic diagram in which positions of the LEDs 13b and the light-receiving devices 13d constituting the photometric apparatus 13 and of the reaction vessels 5 are viewed from the inside of the cuvette wheel 4 with the reaction vessels 5 being arranged in a straight line. The arrow shown in FIG. 3 indicates a movement direction of the reaction vessels 5 by the rotation of the cuvette wheel 4.

The reaction vessel 5 is a vessel called a cuvette having a rectangular cylinder shape and made of an optically transparent material that can transmit 80% or more of analysis light (e.g., 340-800 nm) emitted from the photometric apparatus 13. Such transparent material includes glass including heat-resistant glass, cyclic olefin, and polystyrene. Reagents from the reagent vessels 2a and 3a on the reagent tables 2 and 3 are dispensed into the reaction vessels 5 by reagent dispensing systems 8 and 9 that are located nearby. In the reagent dispensing systems 8 and 9, probes 8b and 9b for dispensing reagents are attached to arms 8a and 9a that are rotated in the horizontal plane in the direction along the arrow. The reagent dispensing systems 8 and 9 include a washing unit that washes the probes 8b and 9b using washing water.

As shown in FIG. 1, the specimen-vessel transferring system 10 moves and transfers arranged racks 11 one by one in the direction along the arrow. The rack 11 holds specimen vessels 11a that contain specimens. Every time the rack 11 transferred by the specimen vessel transferring system 10 stops moving, the specimens contained in the specimen vessels 11a are dispensed into each of the reaction vessels 5 by a specimen dispensing system 12 that includes an arm 12a that can be rotated horizontally and a probe 12b. The specimen dispensing system 12 includes a washing unit that washes the probe 12b using washing water.

The photometric apparatus 13 is an optical system for analyzing a liquid sample in the reaction vessel 5 in which the reagent and the specimen have been reacted with analysis light (e.g., 340-800 nm) transmitted through the liquid sample. As shown in FIGS. 1 and 2, the photometric apparatus 13 includes the LED array 13a, the light-receiving device array 13c, and a photometric control unit 13f.

Figure 4:
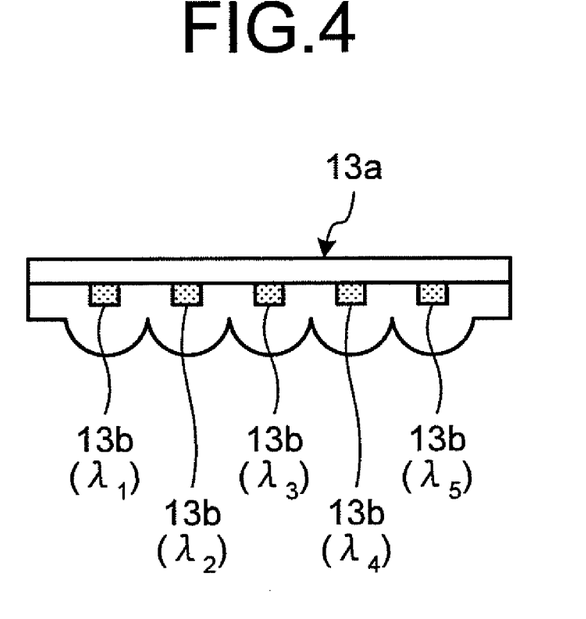
FIG. 4 is a diagram illustrating an arrangement order of wavelengths of light of different wavelengths emitted by LEDs constituting an LED array.

As shown in FIGS. 3 and 4, in the LED array 13a, the LEDs 13b each emitting light of different wavelengths (wavelengths $\lambda 1$-$\lambda 5$) are arranged in an array. The LEDs 13b are arranged in a manner such that the LEDs 13b, starting from the left to the right, emit light of the wavelength $\lambda 1$, $\lambda 2$, $\lambda 3$, $\lambda 4$, and $\lambda 5$, respectively. Furthermore, as shown in FIG. 3, in the LED array 13a, length L along the arrangement direction of the LEDs 13b is shorter than the arrangement pitch P of the reaction vessels 5 so that light of different wavelengths (wavelengths $\lambda 1$-$\lambda 5$) crosses the liquid samples contained in the passing reaction vessels 5.

In the light-receiving device array 13c, the light-receiving devices 13d, which receive light of different wavelengths emitted from the respective LEDs 13b, are located opposing to the LEDs 13b, with the reaction vessels 5 on the cuvette wheel 4 interposed inbetween. The light-receiving device array 13c includes a stray-light blocker 13e such as an interference filter that prevents the entering of stray light emitted from the LED 13b adjacent to the corresponding LED 13b. The stray-light blocker 13e is arranged on a front surface of each light-receiving device 13d, i.e., on a light-receiving side. For example, the light-receiving devices 13d can be a photodiode.

The photometric control unit 13f controls light-on of the LEDs 13b in the LED array 13a, optically measures the amount of light received by the light-receiving devices 13d, and outputs a light signal corresponding to the amount of light received to the control unit 17.

The washing system 14 sucks out and discharges the liquid sample in the reaction vessel 5 using its nozzle 14a and then repeats the injection and suction of washing liquids such as detergents and washing water on the reaction vessel 5 using the nozzle 14a, so that the reaction vessel 5 that has been optically measured by the photometric apparatus 13 is cleaned.

The first stirrer 15 and the second stirrer 16 stir a dispensed specimen and reagent using stir bars 15a and 16a so that the specimen and the reagent react.

The control unit 17 includes a micro computer or the like that has calculation, memory, control, and clock functions and other functions. The control unit 17 is connected with the reagent tables 2 and 3, the driving control unit 6, the reagent dispensing systems 8 and 9, the specimen-vessel transferring system 10, the specimen dispensing system 12, the photometric apparatus 13, the washing system 14, the stirrers 15 and 16, an input unit 18, and a display unit 19, and the like. The control unit 17 controls operations of these components above and obtains light absorbance based on a light signal that is input from the photometric control unit 13f and corresponds to the amount of light received for each wavelength of light. On the basis of the light absorbance, the control unit 17 analyzes a constituent concentration and the like of a specimen. Furthermore, when it is determined that the lot of the reagent is different or that the expiration date has expired on the basis of information read from data on the identification-code label attached to the reagent vessels 2a and 3a, the control unit 17 controls the automatic analyzer 1 to stop performing the analysis process or the control unit 17 gives out a warning to operators.

The input unit 18 is used for inputting examination items and wavelengths for a photometry corresponding to the measurement item of a specimen, i.e., a specification of the LED 13b to be used, into the control unit 17. For example, the input unit 18 can be a keyboard or a mouse. The display unit 19 is used for displaying analysis contents, analysis results, warnings, or the like. The display unit 19 can be a display panel or the like In the automatic analyzer 1 configured as above, the first reagents in the reagent vessels 2a are sequentially dispensed by the reagent dispensing system 8 into the reaction vessels 5 that are transferred along the circumferential direction by the cuvette wheel 4 intermittently rotating. After the first reagents are dispensed into the reaction vessels 5, the specimens in the specimen vessels 11a held in the rack 11 are sequentially dispensed by the specimen dispensing system 12 into the reaction vessels 5. After the specimens are dispensed into the reaction vessels 5, the reaction vessels 5 are stirred by the first stirrer 15 every time the cuvette wheel 4 stops its intermittent rotation, so that the first reagent and the specimen react. After the first reagent and the specimen are stirred, the second reagents in the reagent vessels 3a are sequentially dispensed by the reagent dispensing system 9 into the reaction vessels 5. Then, every time the cuvette wheel 4 stops its intermittent rotation, the reagent vessels 5 are stirred by the second stirrer 16, so that the reaction is further facilitated.

With the photometric apparatus 13, the length L along the arrangement direction of the LEDs 13b in the LED array 13a is shorter than the arrangement pitch P of the reaction vessels 5. Therefore, when the cuvette wheel 4 is intermittently rotated in the photometric apparatus 13, all reaction vessels 5 that are transferred by seven units pass the LED array 13a. Thus, with the photometric apparatus 13, liquid samples contained in seven reaction vessels 5 cross light of different wavelengths (wavelengths $\lambda 1$-$\lambda 5$) emitted from the LEDs 13b, and therefore optical characteristics of the liquid samples are measured with the light of different wavelengths.

In conventional automatic analyzers, the light sources and the light-receiving devices are located opposing each other and along the arrangement direction. The center angles among the light sources are the same as the center angles among the reaction vessels set on the cuvette wheel. In contrast, in the automatic analyzer 1, all seven reaction vessels 5 transferred by one intermittent rotation can be measured with light of different wavelengths. Furthermore, the photometric apparatus 13 uses a semiconductor light source, i.e., LED, as a light source. In this manner, the photometric apparatus 13 itself can be downsized and also the cuvette wheel 4 can be downsized, which allows the automatic analyzer 1 as a whole to be downsized.

In general, the automatic analyzer 1 measures optical characteristics of a liquid sample contained in the reaction vessel 5 with combinations of light of two different wavelengths based on measurement items. For example, suppose that combinations of light of two different wavelengths for measurements are ($\lambda 1$, $\lambda 2$), ($\lambda 2$, $\lambda 3$), ($\lambda 3$, $\lambda 4$), and ($\lambda 4$, $\lambda 5$). In this case, in the LED array 13a in FIG. 4 where the LEDs 13b are arranged in a way that the wavelengths of emitted light are $\lambda 1$, $\lambda 2$, . . . , $\lambda 5$, light emitted from an adjacent LED 13b can possibly enter the light-receiving device 13d that is not at the opposition position as stray light.

Figure 5:
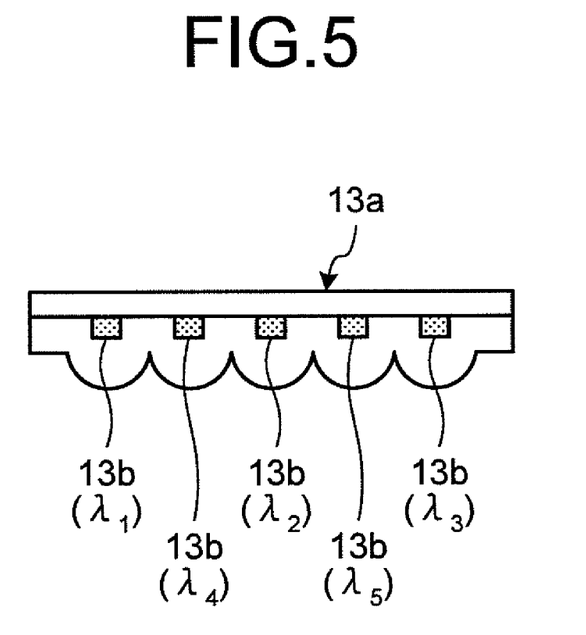
FIG. 5 is a diagram illustrating another arrangement order of wavelengths of light of different wavelengths emitted by LEDs constituting an LED array.

In order to prevent the entering of such stray light, the LEDs 13b in the LED array 13a are arranged in a manner such that the LEDs 13b, starting from the left to the right, emit light of the wavelength $\lambda 1$, $\lambda 4$, $\lambda 2$, $\lambda 5$, and $\lambda 3$, respectively, as shown in FIG. 5. In this manner, at least one light source that is not used for a measurement is located between a combination of light sources used for the measurement. With the photometric apparatus 13 where the LEDs 13b are arranged as described, the measurement of optical characteristics is not affected by stray light, and therefore analysis accuracy of the automatic analyzer 1 is improved.

Figure 6:
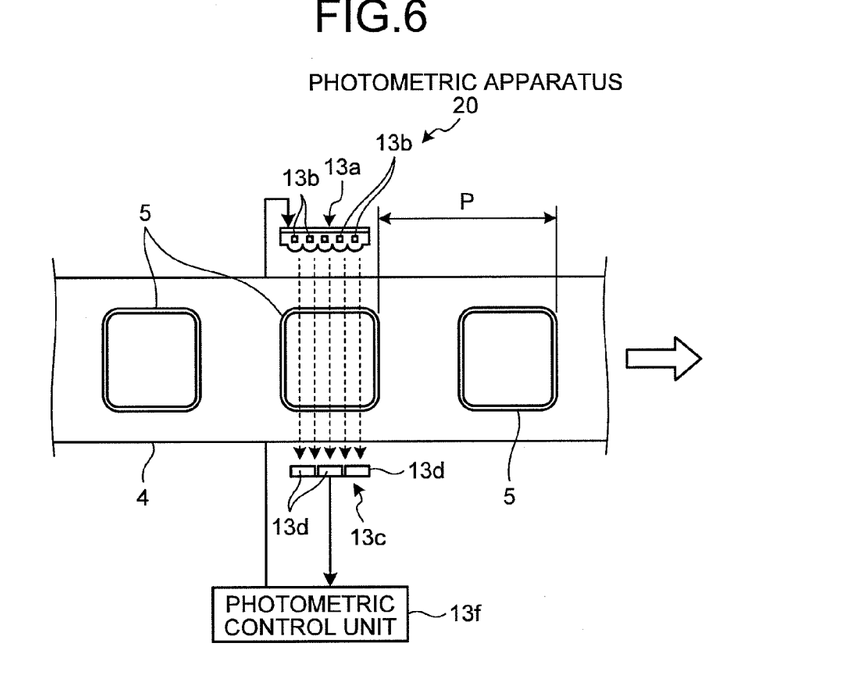
FIG. 6 is a schematic diagram in which positions of LEDs and light-receiving devices constituting a photometric apparatus in accordance with a second embodiment and of reaction vessels are viewed from the inside of a cuvette wheel with the reaction vessels being arranged in a straight line.

A photometric apparatus and an automatic analyzer in accordance with a second embodiment of the present invention are described in detail with reference to drawings. In the photometric apparatus in accordance with the first embodiment, the number of light sources is the same as the number of light-receiving devices. In contrast, in a photometric apparatus in accordance with the second embodiment, the number of light-receiving devices is smaller than the number of light sources. FIG. 6 is a schematic diagram in which positions of LEDs and light-receiving devices constituting a photometric apparatus and of reaction vessels are viewed from the inside of a cuvette wheel with the reaction vessels being arranged in a straight line. Although the configuration of the photometric apparatus differs depending on the parts, an automatic analyzer in accordance with the second embodiment or other embodiments described later has substantially the same configuration as the automatic analyzer and the photometric apparatus in accordance with the first embodiment, and the same components have the same numerals.

As shown in FIG. 6, a photometric apparatus 20 in accordance with the second embodiment includes the LED array 13a, the light-receiving device array 13c, and the photometric control unit 13f. The LED array 13a is the LED array 13a shown in FIG. 5 where the LEDs 13b emit, starting from the left to the right, light of wavelengths $\lambda 1$, $\lambda 4$, $\lambda 2$, $\lambda 5$, and $\lambda 3$, respectively. The light-receiving device array 13c includes three light-receiving devices 13d: the light-receiving device 13d that is located opposing the LED 13b emitting light of wavelength λ1, the light-receiving device 13d that is located opposing to the LEDs 13b emitting light of wavelengths λ4 and λ2, and the light-receiving device 13d that is located opposing to the LEDs 13b emitting light of wavelengths λ5 and λ3. The photometric apparatus 20 measures optical characteristics of liquid samples contained in the reaction vessels 5 with combinations of light of two different wavelengths (λ1, λ2), (λ2, λ3), (λ3, λ4), and (λ4, λ5).

When the photometric apparatus 20 measures optical characteristics of liquid samples, light of two different wavelengths never enters the same light-receiving device 13d simultaneously. In addition to the advantage provided in the first embodiment, the photometric apparatus 20 can measure optical characteristics of liquid samples with three light-receiving devices 13d, meaning that the number of light-receiving devices can be reduced. Furthermore, of five LEDs 13b, at least one light source not being used for a measurement of optical characteristics (not being light-on) is located between two LEDs 13b being used for the measurement (being light-on), and the space between two LEDs 13b becomes wider. Therefore, with the photometric apparatus 20, light emitted from the LEDs 13b enters only light-receiving devices 13d located at opposing positions, and light emitted from other LEDs 13b does not enter the light-receiving devices 13d as stray light. As a result, photometry accuracy is improved.

Figure 7:
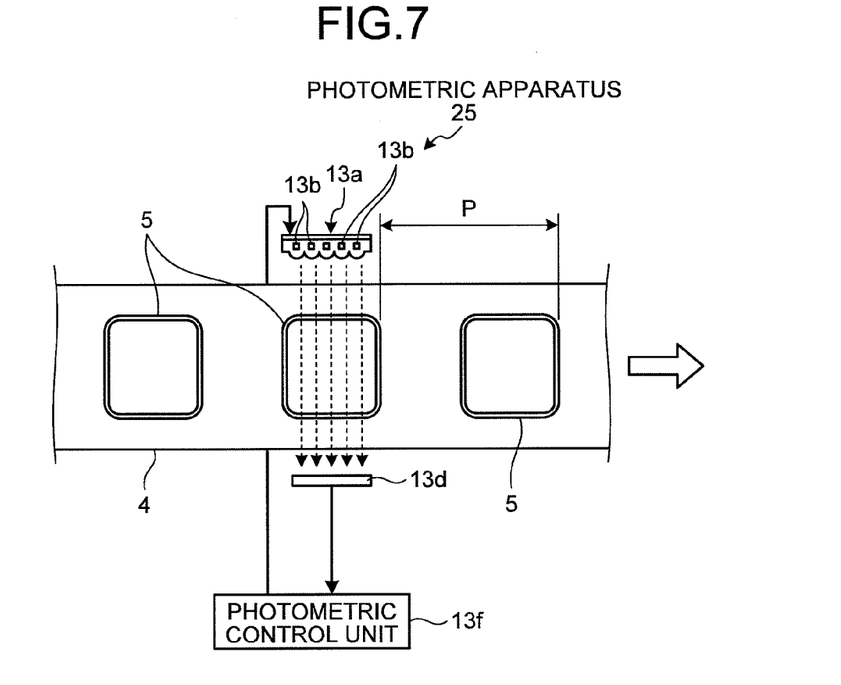
FIG. 7 is a schematic diagram in which positions of LEDs and light-receiving devices constituting a photometric apparatus in accordance with a third embodiment, and of reaction vessels are viewed from the inside of a cuvette wheel with the reaction vessels being arranged in a straight line.
Figure 8:
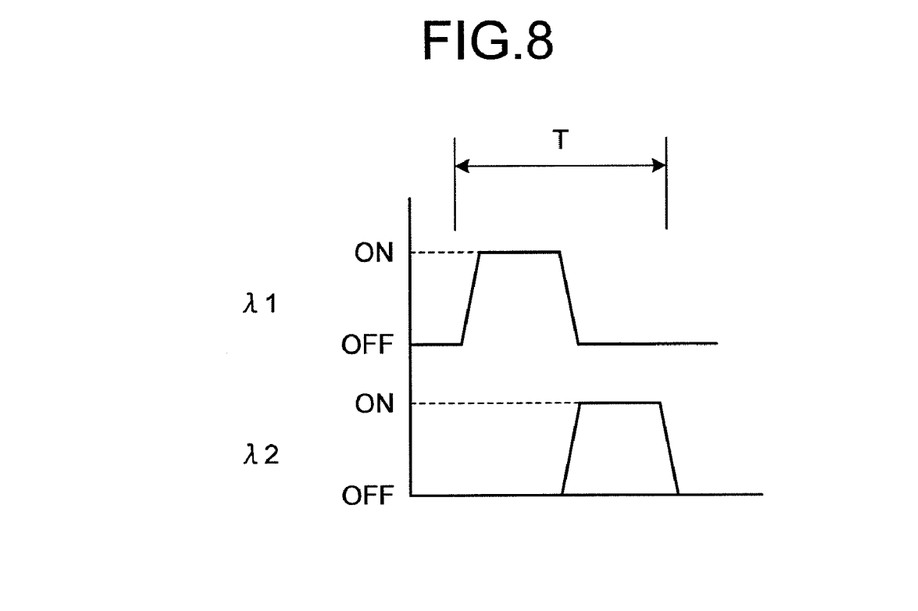
FIG. 8 is a diagram illustrating the light-on timing of two light sources used for measuring optical characteristics during one light-on cycle.

A photometric apparatus and an automatic analyzer in accordance with a third embodiment of the present invention are described in detail with reference to drawings. A photometric apparatus in accordance with the second embodiment uses five light sources and three light-receiving devices. In contrast, a photometric apparatus in accordance with the third embodiment uses one light-receiving device. FIG. 7 is a schematic diagram in which positions of LEDs and light-receiving devices constituting a photometric apparatus in accordance with a third embodiment, and of reaction vessels are viewed from the inside of a cuvette wheel with the reaction vessels being arranged in a straight line. FIG. 8 is a diagram illustrating a light-on timing of two light sources used for measuring optical characteristics during one light-on cycle.

As shown in FIG. 7, a photometric apparatus 25 in accordance with the third embodiment includes the LED array 13a, the light-receiving device 13d, and the photometric control unit 13f. When optical characteristics of liquid samples contained in the reaction vessels 5 are measured, the photometric control unit 13f controls the LED array 13a and turns on light of five LEDs 13b on a time-division basis.

For example, when the photometric apparatus 25 measures optical characteristics of liquid samples contained in the reaction vessels 5 with a combination of light of two optical wavelengths (λ1, λ2), the photometric control unit 13f controls light-on (ON or OFF) of the LEDs 13b emitting light of wavelength λ1 and the LED 13b emitting light of wavelength λ2 in one light-on cycle T. Meanwhile, the photometric control unit 13f keeps the other three LEDs 13b respectively emitting light of wavelengths λ3-λ5 OFF.

In addition to the advantage provided in the first embodiment, the photometric apparatus 25 turns on the LEDs 13b used for measuring optical characteristics on a time-division basis, and the number of light-receiving devices can be reduced to be one.

Although the automatic analyzer described above uses two reagent tables and two types of reagents, the number of reagent tables may be one. A reagent vessel for the first reagent and a reagent vessel for the second reagent may be located on the one reagent table, or one type of a reagent vessel may be located on each reagent table.

Furthermore, although the automatic analyzer described above uses a semiconductor light source as an LED, the automatic analyzer may use a semiconductor laser. Furthermore, the embodiment does not limit the number of reaction vessels 5 that cross the light emitted by the LED array 13a when the cuvette wheel 4 is intermittently rotated one revolution and does not limit the number of LEDs 13b and light-receiving devices 13d constituting the photometric apparatus.

A photometric apparatus according to an embodiment of the present invention includes a plurality of light sources that is arranged along a movement direction of vessels and emits light of different wavelengths, and a plurality of light-receiving devices that is located at opposing positions to the light sources with the vessels interposed inbetween and receives light of different wavelengths emitted from the light sources. The arrangement length of the light sources along the movement direction of the vessels is shorter than the arrangement pitch of the vessels. An automatic analyzer of the present invention includes the photometric apparatus. Therefore, the photometric apparatus and the automatic analyzer of the present invention can measure optical characteristics of liquids stored in the reaction vessels with light of different wavelengths, the reaction vessels being transferred and crossing light sources when a cuvette wheel is rotated by one intermittent rotation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A photometric apparatus that is used in an automatic analyzer that measures an optical characteristic of liquids contained in vessels with light of different wavelengths while transferring the vessels, the photometric apparatus comprising:

light sources that are arranged in a circle, concentric to a movement direction of the vessel and respectively emit light of different wavelengths in a direction perpendicular to the movement direction of the vessel; and light-receiving devices that are located opposing to the light sources with the vessel interposed in between and receive light of different wavelengths emitted from the light sources, wherein an arrangement length of the light sources along the movement direction of the vessel is shorter than an arrangement pitch of the vessel.

2. The photometric apparatus according to claim 1, wherein
the number of the light-receiving devices is the same as the number of the light sources.

3. The photometric apparatus according to claim 1, wherein
at least one of the light sources is located between a combination of the light sources that is specified according to a measurement item to be used for measuring the optical characteristic.

4. The photometric apparatus according to claim 1, wherein
the number of the light-receiving devices is smaller than the number of the light sources.

5. The photometric apparatus according to claim 4, wherein
the light sources are turned on on a time-division basis when light emitted from the light sources enters the same light-receiving device, so that measurement of the optical characteristic with the light of different wavelengths is completed within a period of time during which one of the vessels crosses space between the light sources and the light-receiving device.

6. The photometric apparatus according to claim 1, wherein
the light sources are semiconductor light sources.

7. An automatic analyzer that measures an optical characteristic of liquids contained in vessels with light of different wavelengths while transferring the vessels, the automatic analyzer comprising:
the photometric apparatus according to claim 1.

* * * * *